US012642926B1

(12) United States Patent
Kaczkowski et al.

(10) Patent No.: US 12,642,926 B1
(45) Date of Patent: Jun. 2, 2026

(54) FLUID INHALATION DEVICE

(71) Applicant: Kaczkowski, Inc., Little Rock, AR (US)

(72) Inventors: Michael D Kaczkowski, Little Rock, AR (US); Zigmond R. Gustafson, Jacksonville, AR (US)

(73) Assignee: Kaczkowski, Inc., Little Rock, AR (US)

( * ) Notice: Subject to any disclaimer, the term of this patent is extended or adjusted under 35 U.S.C. 154(b) by 0 days.

(21) Appl. No.: 19/390,533

(22) Filed: Nov. 15, 2025

(51) Int. Cl.
| | |
|---|---|
| *A61M 15/00* | (2006.01) |
| *A24B 15/167* | (2020.01) |
| *A24F 7/00* | (2006.01) |
| *A24F 42/20* | (2020.01) |
| *A24F 42/60* | (2020.01) |

(52) U.S. Cl.
CPC ....... *A61M 15/0093* (2014.02); *A24B 15/167* (2016.11); *A24F 7/00* (2013.01); *A24F 42/20* (2020.01); *A24F 42/60* (2020.01)

(58) Field of Classification Search
CPC ........ A61M 15/0093; A61M 11/00–08; A61M 15/0091–0096; A24B 15/167; A24F 7/00; A24F 42/20; A24F 42/60; B05B 17/00–085
See application file for complete search history.

(56) References Cited

U.S. PATENT DOCUMENTS

| | | | |
|---|---|---|---|
| 3,097,645 | A | 7/1963 | Lester |
| 4,054,622 | A | 10/1977 | Lester |
| 4,251,033 | A | 2/1981 | Rich et al. |
| 4,284,089 | A | 8/1981 | Ray |
| 4,588,129 | A | 5/1986 | Shanks |
| D299,066 | S | 12/1988 | Newell et al. |
| 4,792,097 | A * | 12/1988 | Kremer, Jr. ........... B05B 7/0012 |
| | | | 261/78.2 |
| 4,793,366 | A | 12/1988 | Hiii |
| 4,800,903 | A | 1/1989 | Ray et al. |
| 4,917,120 | A | 4/1990 | Hill |
| 5,054,477 | A | 10/1991 | Terada et al. |
| 5,167,242 | A | 12/1992 | Turner et al. |
| 5,388,574 | A | 2/1995 | Ingebrethsen |
| 5,400,808 | A | 3/1995 | Turner et al. |
| 5,533,497 | A | 7/1996 | Ryder |
| 6,089,228 | A | 7/2000 | Smith et al. |

(Continued)

OTHER PUBLICATIONS

U.S. Appl. No. 18/984,287, filed Dec. 17, 2024.

(Continued)

*Primary Examiner* — Elliot S Ruddie
(74) *Attorney, Agent, or Firm* — EVAN LAW GROUP LLC

(57) ABSTRACT

A fluid inhalation device, comprises a casing having therein a fluid reservoir, a fluid-air outlet connected to a top end of the fluid reservoir, a vacuum channel, having a bottom end connected to a bottom end of the fluid reservoir, an air duct having an air inlet at a first air duct end, and a nozzle connected to a second air duct end through a nozzle throat and connected to the fluid reservoir through a nozzle exit, a top end of the vacuum channel is connected to the nozzle. The fluid inhalation device may also include a filling port, fluidly connected to the fluid reservoir; and/or one or both of an air duct valve, and the fluid-air channel valve.

25 Claims, 5 Drawing Sheets

(56)  References Cited

U.S. PATENT DOCUMENTS

| | | | |
|---|---|---|---|
| D514,222 S | 1/2006 | Anderson et al. | |
| D660,956 S | 5/2012 | Zuyderhoudt | |
| D661,795 S | 6/2012 | Clarke et al. | |
| D681,267 S | 4/2013 | Touzjian | |
| D721,972 S | 2/2015 | Brewer et al. | |
| D762,003 S | 7/2016 | Lomell | |
| D788,697 S | 6/2017 | Verteor et al. | |
| D801,579 S | 10/2017 | Nyaggah | |
| D801,581 S | 10/2017 | Scott et al. | |
| D808,073 S | 1/2018 | Leidel | |
| D844,235 S | 3/2019 | Cividi | |
| D850,711 S | 6/2019 | He et al. | |
| D854,741 S | 7/2019 | Smith | |
| D869,085 S | 12/2019 | Campbell et al. | |
| D903,937 S | 12/2020 | Chimbuya et al. | |
| D984,730 S | 4/2023 | Boham et al. | |
| D985,187 S | 5/2023 | Boham et al. | |
| 11,772,109 B2 | 10/2023 | Zarfl | |
| 12,458,765 B1 * | 11/2025 | Kaczkowski | A24F 40/10 |
| 2003/0136399 A1 | 7/2003 | Foley et al. | |
| 2023/0263970 A1 | 8/2023 | Kaczkowski | |
| 2023/0264214 A1 | 8/2023 | Kaczkowski | |

OTHER PUBLICATIONS

U.S. Appl. No. 19/065,937, filed Apr. 16, 2025.
U.S. Appl. No. 19/065,937, filed Jun. 20, 2025.
U.S. Appl. No. 19/065,937, filed Jul. 28, 2025.
U.S. Appl. No. 19/390,533, filed Feb. 5, 2026.

* cited by examiner

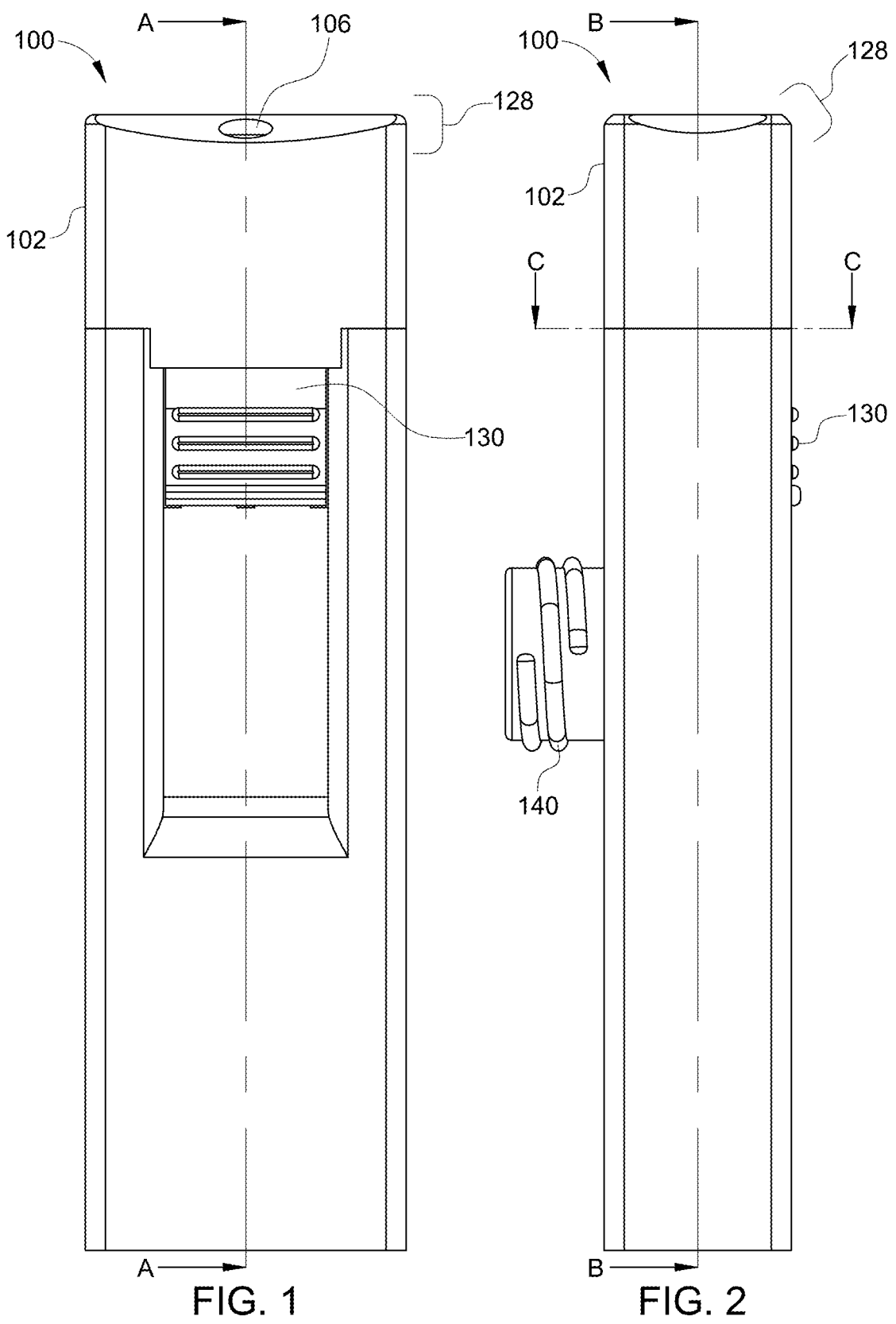
FIG. 1        FIG. 2

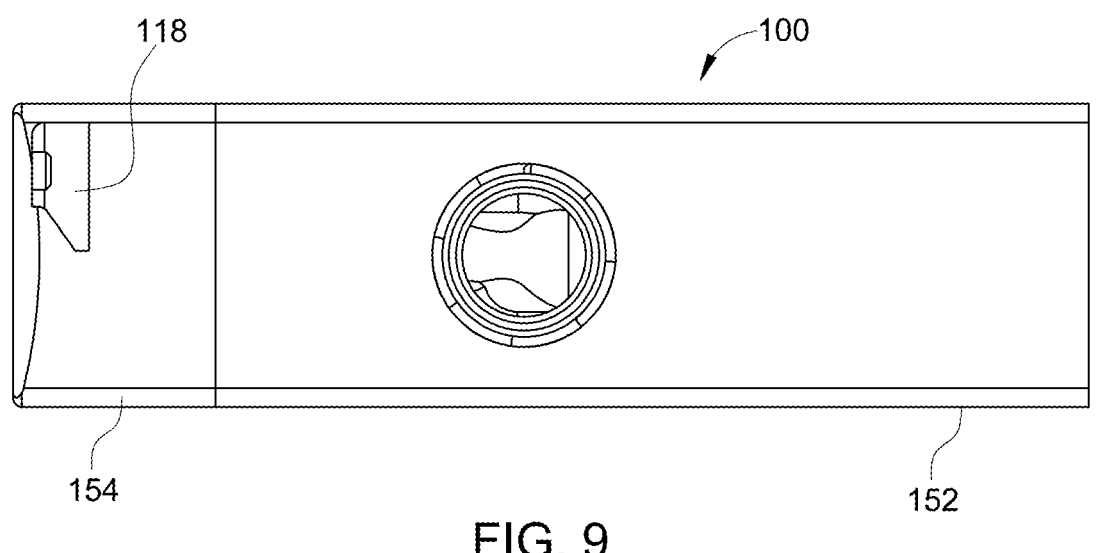
FIG. 9
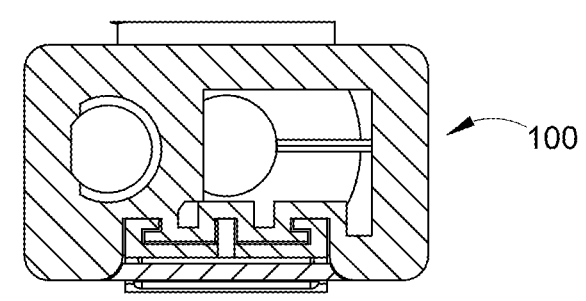
FIG. 10
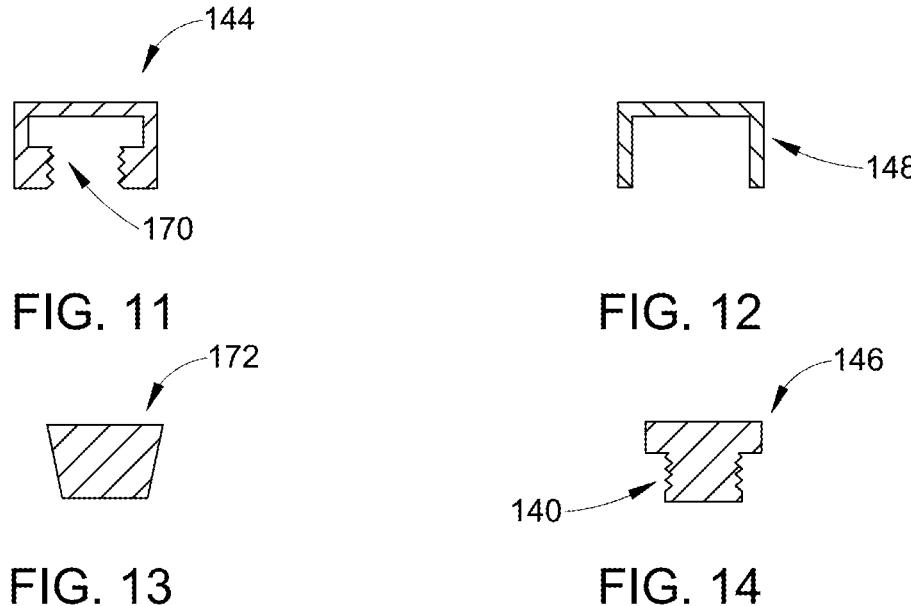
FIG. 11             FIG. 12
FIG. 13             FIG. 14

FLUID INHALATION DEVICE

BACKGROUND

A variety of devices are known for atomizing and propelling a liquid. Examples include spray pump bottles, such as those which use an internal propellant (for example spray paint cans, hair sprays, air fresheners and inhalers for asthma medications), or which include a hand pump (hand pump bottles used for window glass cleaning and fabric stain removers). Some devices, such as nicotine vaping devices (E-cigarettes) use heat to vaporize a fluid, that may form an aerosol, which is then inhaled by a user. A nebulizer, a device for producing a fine spray of liquid, and used for inhaled medication, are often powered by compressed air, either from a compressed gas tank or produced using an electric pump.

SUMMARY

The present invention includes a fluid inhalation device, comprising a casing having therein a fluid reservoir, a fluid-air outlet connected to a top end of the fluid reservoir, a vacuum channel, having a bottom end connected to a bottom end of the fluid reservoir, an air duct having an air inlet at a first air duct end, and a nozzle connected to a second air duct end through a nozzle throat and connected to the fluid reservoir through a nozzle exit, a top end of the vacuum channel is connected to the nozzle. The fluid inhalation device may also include a filling port, fluidly connected to the fluid reservoir; and/or one or both of an air duct valve, and the fluid-air channel valve.

Definitions

"Connected" and "connects" means fluidly connected or fluidly connects, respectively, which allow for the flow of fluids, including gases (such as air) and liquids (such as water, ethanol and liquid mixtures, solutions, dispersions, suspensions and emulsions).

"Nozzle" means a channel or chamber where air may mix with another fluid, to form a fluid-air mixture.

The spatial prepositions such as "top," "bottom," "above," and "below" which describe the relative position of structural elements in space, are in reference to the orientation of the device (such as the fluid inhalation device) during use. For example, during use the fluid inhalation device is always oriented with the fluid reservoir bottom end below the remainder of the fluid reservoir.

The phrase "configured for human mouth powered operation" means operated by suction by mouth on a mouth piece at a pressure of −0.14 to −0.36 PSI, negative pressure relative to atmospheric pressure.

BRIEF DESCRIPTION OF THE DRAWINGS

FIG. 1 illustrates a front view of a fluid inhalation device.

FIG. 2 illustrates a side view of a fluid inhalation device.

FIG. 9 illustrates a back view of a fluid inhalation device.

FIG. 10 illustrates a cross-section interior view of a fluid inhalation device along plane C-C in FIG. 2.

FIG. 11, FIG. 12, FIG. 13 and FIG. 14 each illustrate different types of closures for sealing the filling port of various fluid inhalation devices.

DETAILED DESCRIPTION

Figures 3, 4:
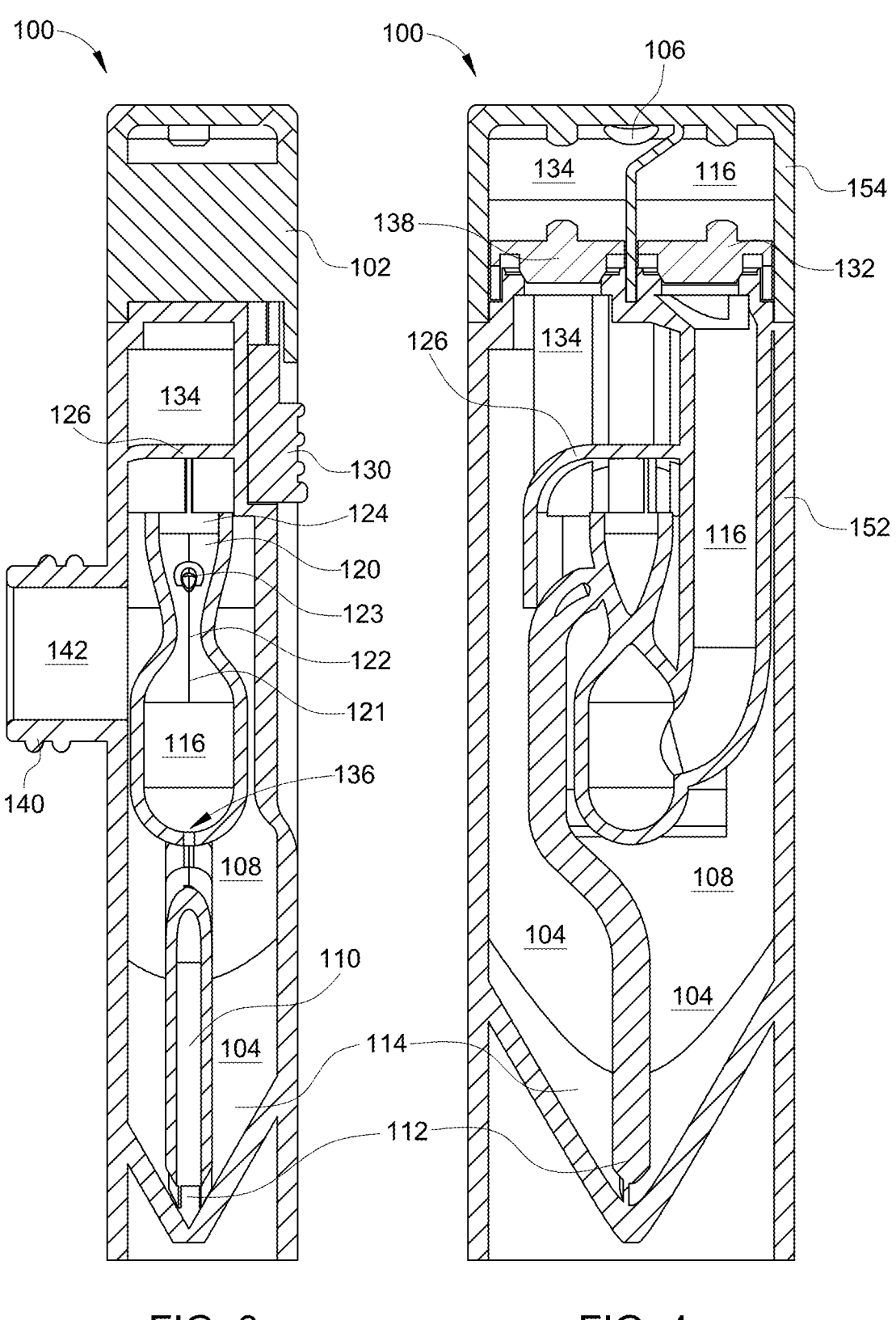
FIG. 3 illustrates a cross-section interior view of a fluid inhalation device along plane A-A in FIG. 1.
FIG. 4 illustrates a cross-section interior view of a fluid inhalation device along plane B-B in FIG. 2.

A fluid inhalation device provides a fluid-air mixture to the user, when the device is powered by mouth suction of the user. No other power source is needed to operate the device, neither a pump nor a heater. When mouth suction is used to power the device, a stream of air enters the device through an air inlet, travels through an air duct and into a nozzle. Within the nozzle, the reduced pressure created by the flowing air sucks liquid from a fluid reservoir through a vacuum channel. Within the nozzle, the liquid is broken up into droplets, and flows out of the nozzle. The flowing air transports the droplets up and through the fluid-air outlet and into the user's mouth, thereby delivering the fluid to the user. Large droplets and bulk liquid are too heavy to be transported out of the device by the moving air, and return back into the fluid reservoir. The device is configured to be used in an upright position, so that the liquid remains at the bottom of the fluid reservoir; the operation of the device makes use of gravity to contain liquid in desired locations, such as at the bottom of the fluid reservoir. In a variation, the nozzle exit directly opens into the fluid reservoir, for example above the level of the liquid contained therein. In a variation, a spray shield is used to intercept large droplets to prevent them from traveling into the user's mouth, for example in the fluid reservoir, or present between the nozzle exit and the fluid-air outlet, or the spray shield may block a straight line between the nozzle exit and the fluid-air outlet. In a variation, a fluid-air mixture channel is used to increase the distance between the nozzle and the fluid-air outlet, for example by connecting the nozzle or the fluid reservoir to the fluid-air outlet, making use of gravity to prevent large droplets from traveling into the user's mouth. In a variation, a mouth piece contains the fluid-air mixture outlet. In a variation, the nozzle exit opens into the fluid-air mixture channel. Each of these variations may be used alone, or in combinations and permutations. Such devices are described in U.S. Pat. No. 12,458,765.

These fluid inhalation devices deliver fluid to the user without heating, as occurs in vaping devices. By avoiding heating, there is no damage or chemical change to the components of the liquid, not only preventing destruction of the ingredients, but also avoid the formation of undesirable, bad-tasting or dangerous chemicals, for example carbon monoxide, nitrogen oxides, carbon dioxide, nitrosamines, aldehydes, and volatile organic compounds (VOCs). The fluid inhalation devices may be manufactured completely out of plastic using, for example, additive manufacture, and thus may avoid introducing metal into the fluid-air mixture inhaled by the user.

When fluid is present in the fluid inhalation device, in the fluid reservoir, and the device is not held upright in the hand of the user, or if the user is jostled while holding the device, the liquid may spill or leak out of the device, flowing or splashing out through the air inlet, and/or the fluid-air outlet.

Furthermore, it may be difficult to load fluid into the fluid reservoir, either through the air inlet or fluid-air outlet, because the size of these orifices is small.

The present invention includes a fluid inhalation device which includes channel valves, a fluid-air mixture channel valve and an air duct valve, each of which may be opened or closed. When in a closed position, the fluid-air mixture channel is closed, and/or the air duct is closed, preventing fluid from leaking or spilling from the device. When the valves are in the open position, the fluid inhalation device may be used normally.

The present invention includes a fluid inhalation device which includes a filling port with an optional fluid port stem, which has a larger opening that the air inlet or fluid-air outlet, and which is fluidly connected to the fluid reservoir. This allows for easy filling of the fluid inhalation device with a liquid. The fluid port may be sealed, for example with a cap or cork, to prevent leakage of fluid during use. In a variation, a fluid inhalation device includes both channel valves and a filling port.

FIG. 1 and FIG. 2 show external views of a fluid inhalation device, for referencing the cross-sections of FIG. 3 and FIG. 4. FIG. 3 and FIG. 4 each illustrates orthogonal cross-section interior views of a first fluid inhalation device, 100, having a casing, 102. The casing has formed therein a fluid reservoir, 104, a fluid-air outlet, 106, a vacuum channel, 110, an air duct, 116, having an air inlet, 118 (not shown), at a first air duct end, and a nozzle, 120. The fluid-air outlet is connected to a top end, 108, of the fluid reservoir. A bottom end, 112, of the vacuum channel is connected to a bottom end, 114, of the fluid reservoir. The nozzle, 120, includes a nozzle throat, 122, and a nozzle exit, 124, with the nozzle throat being connected to a second air duct end, 121, and the nozzle exit being connected to the fluid-air mixture channel, 134, and the fluid reservoir. A top end of the vacuum channel, 123, is connected to the nozzle. Preferably, the nozzle throat is narrower than the nozzle exit, and optionally the nozzle exit directly opens into the fluid reservoir. An optional valve activator, 130, is connected to an optional air duct valve, 132, and an optional fluid-air channel valve, 138. Also illustrated are the optional mouth piece, 128, optional filling port, 142, and optional filling port stem, 140, illustrated with external threads. A fluid return channel, 136, is shown which allows fluid present in the air duct to flow into the fluid reservoir. Also illustrated is that the device may be made from multiple parts, including a removable reservoir, 152, a removable top, 154. An optional spray shield, 126, is also shown.

In use, the fluid inhalation device of FIG. 1 to FIG. 4 contains a liquid in the fluid reservoir. A person (or user) then sucks in air from the fluid-air outlet, using their lips to make a seal around the fluid-air outlet, preferably with the assistance of the optional mouth piece. This suction causes air to flow through the device, entering through the air inlet, traveling through the air duct and through the nozzle. The flowing air has a lower pressure than the ambient air, causing the liquid in the fluid reservoir to flow up through the vacuum channel and into the nozzle. Within the nozzle, the liquid (which may have vaporized in part, due to the reduced pressure within the nozzle) will form a fluid-air mixture and flow out of the nozzle through the nozzle exit and into the fluid-air mixture channel. The fluid-air mixture will then flow out of the top of the fluid reservoir and out of the fluid inhalation device through the fluid-air outlet, into the mouth of the person. The fluid-air mixture will travel through the mouth, and depending on the depth of inhalation by the person, through their throat and into their lungs.

Preferably, the top end of the vacuum channel is connected to the nozzle between the nozzle throat and the nozzle exit. Preferably, the nozzle throat is narrower than the air duct where the air duct connects to the nozzle throat.

Preferably, the composition of the liquid is such that most or all of the liquid remains as a liquid, and is contained in the fluid reservoir when the device is held for use with the bottom of the fluid reservoir closest to the ground. The liquid will atomize, forming droplets of various sizes. The smaller droplet will be carried by the air flow through and out of the device and into the user. The larger droplet, in contrast, having a smaller ratio of surface area to volume, will fall and flow to the bottom of the fluid reservoir, or impact the interior walls of the casing, and flow to the bottom of the fluid reservoir. As shown in FIG. 3 and FIG. 4, the device is configured to provide a very fine mist of the fluid into the mouth of the user when a person uses normal breath inhalation, without the user receiving large droplets or bulk liquid which would be experienced as if a liquid were being sucked into the mouth. Preferably, as shown in FIG. 3 and FIG. 4, the air inlet is located near the top of the fluid inhalation device.

FIG. 3 and FIG. 4 also illustrate additional features: an optional spray shield, 126, and an optional sloping fluid reservoir bottom. The spray shield provides 2 different functions: the spray shield intercepts the largest droplet exiting the nozzle, causing the largest droplet to flow back to the bottom of the fluid reservoir; and the spray shield elongates the flow path, from the nozzle exit to the fluid-air outlet, and causes the flow path to curve, providing more time and opportunity for the largest droplets to fall and/or impact the interior walls of the casing. The sloping fluid reservoir bottom enhances the amount of liquid in the fluid reservoir which is available to be sucked into the vacuum channel.

As shown in FIG. 3 and FIG. 4, the nozzle, 120, of the fluid inhalation device, 100, does not open directly into the fluid reservoir, 104, but rather points upwards and is above the fluid reservoir, placed in a fluid-air mixture channel, 134, which connects the fluid reservoir and the fluid-air outlet, 106. The spray shield, 126, has a curved shape and covers the nozzle exit, 124. Larger droplets which intersect with the spray shield will run down the outer edges of the spray shield and flow back into the fluid reservoir. A liquid which flows into the nozzle from the vacuum channel, 110, which is not atomized, or which is in the form of large droplets which fall down, will flow or fall back into the air duct, and will be returned to the fluid reservoir through a fluid return channel, 136. As shown in FIGS. 3 and 4, the fluid inhalation device is formed of a removable reservoir, 152, which couples to a removable top, 154; as shown, the removable reservoir and removable top snap together. As shown, an optional third part is the valve-activator assembly, which includes the valve activator, 130, connected to air duct valve, 132, and the fluid-air channel valve, 138, with the valve-activator assembly also including optional springs (not illustrated) for maintaining the valves in a closed position when the device is not in use.

Figures 5, 6, 7:
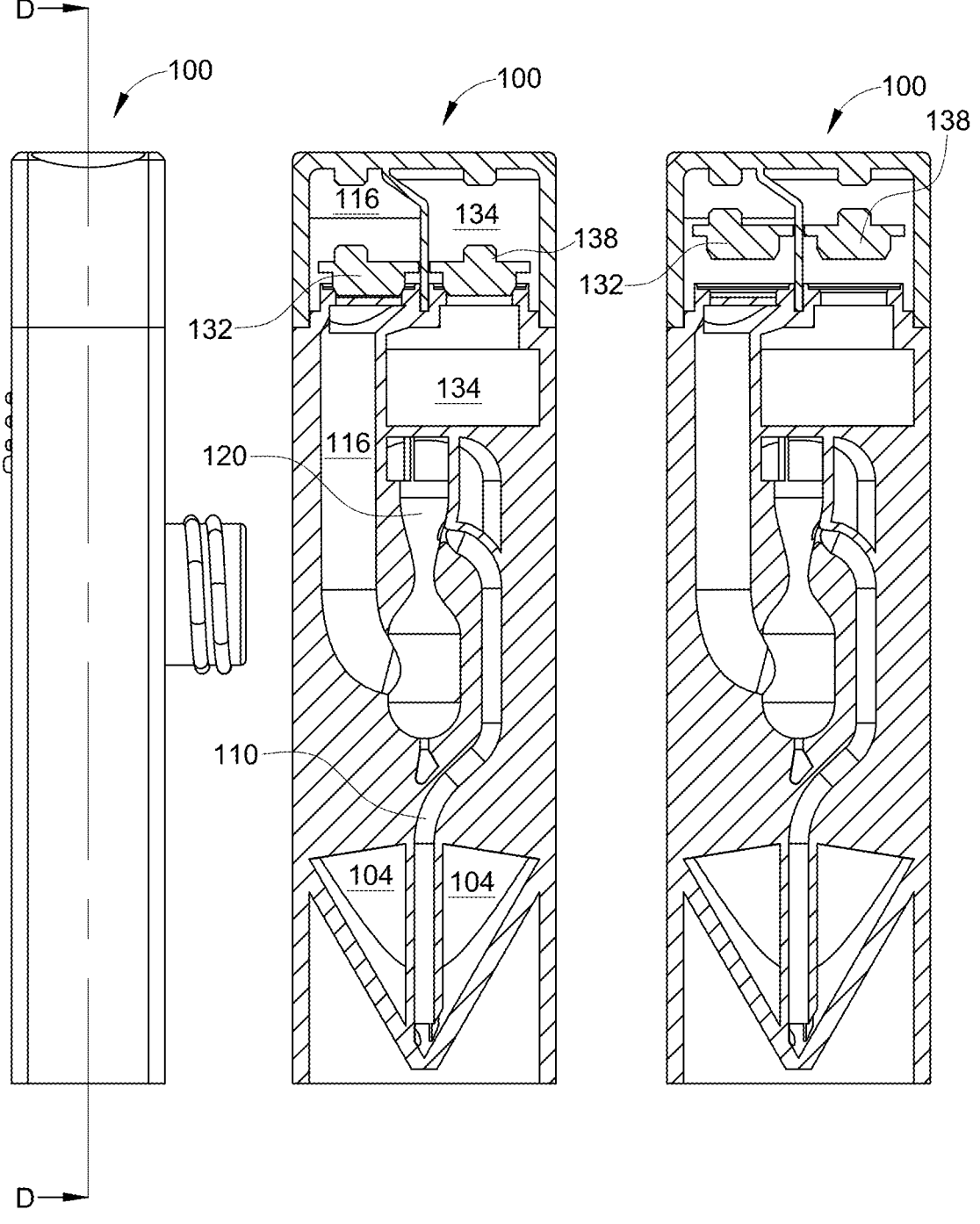
FIG. 5 illustrates a side view of a fluid inhalation device.
FIG. 6 illustrates a cross-section interior view of a fluid inhalation device along plane D-D in FIG. 5, with valves in a closed position.
FIG. 7 illustrates a cross-section interior view of a fluid inhalation device along plane D-D in FIG. 5, with valves in an open position.

FIG. 5 shows an external view of the fluid inhalation device, for referencing the cross-sections of FIG. 6 and FIG. 7. FIG. 6 shows the air duct valve, 132, and the fluid-air channel valve, 138, in a closed position, while FIG. 7 shows the air duct valve, 132, and the fluid-air channel valve, 138, in an open position. The open and closed positioning of the valves is controlled by the valve activator (not shown). When present, the optional springs (not shown) are placed between the top of each valve and the bottom internal surface of a top of the casing, biasing the valves in the closed position.

The mouth piece has a size and length such that the mouth piece is configured to allow a user to insert the mouth piece in the mouth and form a seal, both liquid and gas tight, with the user's lips. A mouth piece has a length of at least 1 cm, preferably at least 1.5 cm, more preferably at least 2 cm. A mouth piece may be at most 6 cm, more preferably at most 5 cm, most preferably at most 4 cm, for example 1 to 6 cm, or 1.5 to 5 cm, or 2 to 4 cm, in length. The opening in the mouth piece preferably has an area of at most 0.75 cm², more preferably at most 0.25 cm², even more preferably at most 0.1 cm² (100 mm²), and even more preferably at most 50 mm², for example 1 to 100 mm², 5 to 50 mm², including 5, 6, 8, 10, 12, 15, 20, 25, 30, 40 and 50 mm², and all ranges therebetween.

Figure 8:
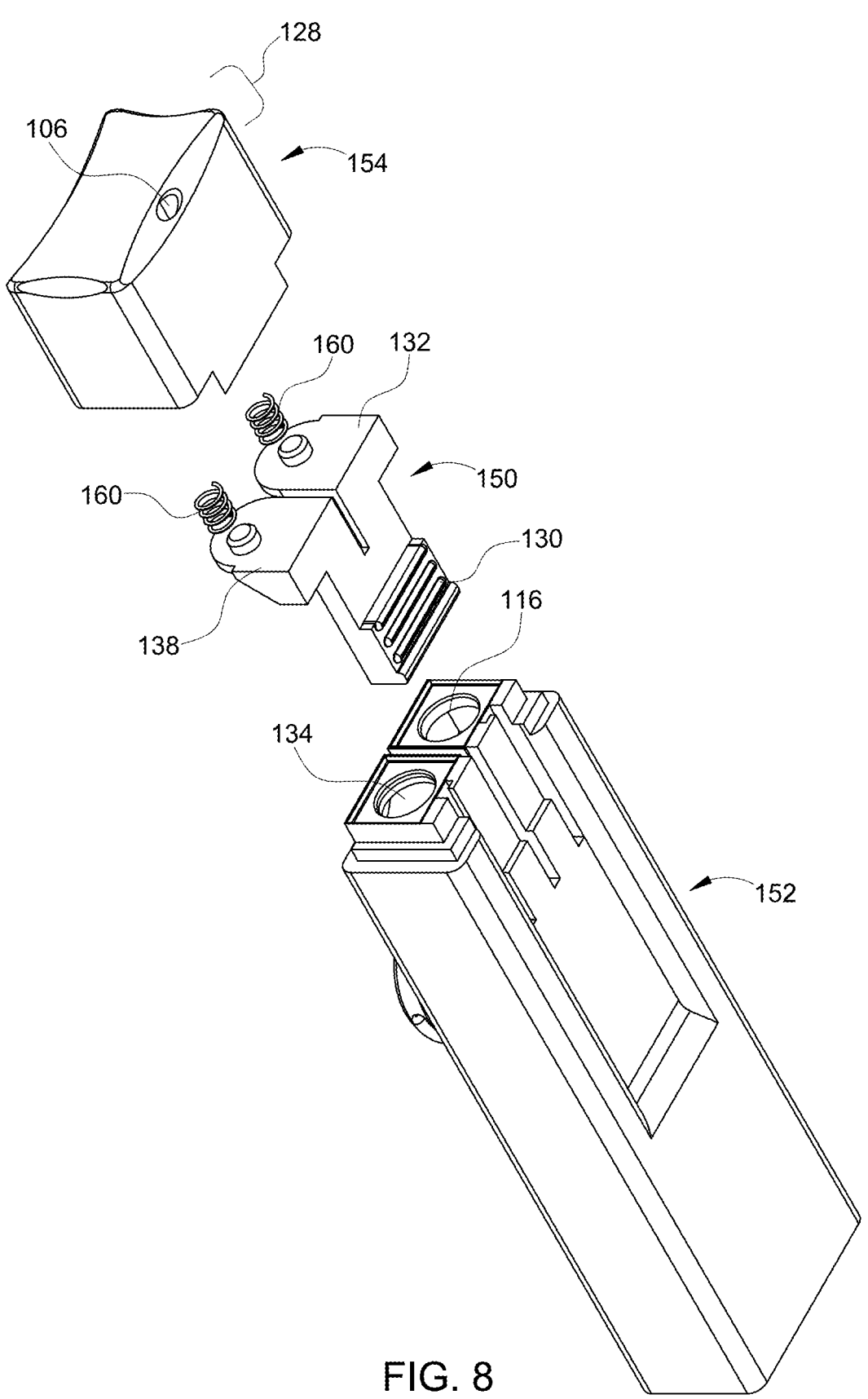
FIG. 8 illustrates a disassembled view of a fluid inhalation device.

An alternate design of a fluid inhalation device including a removable reservoir and a removable top, is shown in a disassembled view in FIG. 8. The fluid inhalation device includes a removable reservoir, 152, and a removable top, 154. The removable reservoir optionally contains a fluid and a breakable seal which maintains the fluid within the removable reservoir prior to assembly of the fluid inhalation device. The removable top includes the fluid-air outlet, 106, which is included in the mouth piece, 128. The removable reservoir includes portions of the air duct, 116, and the fluid-air mixture channel, against which the air duct valve, 132, and the fluid-air channel valve, 138, will seat when the valves are in a closed position. Also shown in the valve-activator assembly, 150, including the air duct valve, 132, and the fluid-air channel valve, 138 and optional springs, 160, for maintaining the valves in a closed position when the device is not in use. Preferably, as shown, both valves are connected to the valve activator, 130, for example by all 3 being a monolithic structure.

FIG. 9 illustrates a back view of a fluid inhalation device, 100, having an air inlet, 118, which opens into an air duct. The air inlet may be placed in a variety of different locations on the exterior of the fluid inhalation device. As illustrated, the air inlet is formed in a removable top, 154, on a back surface adjacent to the top surface of the casing.

FIG. 10 illustrates a cross-section interior view of a fluid inhalation device along plane C-C in FIG. 2.

FIG. 11, FIG. 12, FIG. 13 and FIG. 14 illustrate different types of closures for sealing the optional filling port, and optional filling port stem. FIG. 11 shows a cap, 144, with interior thread, 170, the interior threads being configured to mate with the exterior threads of the filling port stem shown in FIG. 2. FIG. 12 shows a snap cap, 148, configured to snap over and seal a filling port stem, such that threads are not required. FIG. 13 illustrates a stopper, 172, made of flexible and/or elastomeric material, which may be inserted into a filling port or filling port stem. FIG. 14 shows a cap with external threads, 146, which is configured to seal a filling port or filling port stem. With each of these different closures, the fluid inhalation device allows for filling the device with liquid, and then sealing the filling port to prevent any leakage of liquid. When used together with optional valves in a closed position, the resulting fluid inhalation device is both easy to fill with liquid, and can be handled or stored in any position without risk of leakage or evaporation of fluid. When used with the springs, the valves will remain in a closed position, except when open by a user moving the valve activator. The device may include multiple activators, one for each valve, or preferably a single activator connected to both valves.

An alternate design of a fluid inhalation device which is monolithic (or has a unibody construction, other than an optional activator-valve assembly). In a variation, the fluid inhalation device includes means for producing a fluid-air mixture, for example the vacuum channel together with the nozzle. In a variation, the fluid inhalation device includes means for providing a stream of air into the device, for example the air inlet together with the air duct. In a variation, the fluid inhalation device includes means for returning large droplets and bulk fluid from the fluid-air mixture to the fluid reservoir, for example the nozzle exit or other element for producing the fluid-air mixture opening into the fluid reservoir, alternatively a fluid return channel. In a variation, the fluid inhalation device includes means for providing the fluid-air mixture to the fluid-air outlet, such as a connection between the nozzle exit and the fluid-air outlet. In a variation, the fluid inhalation device includes means for preventing large droplets from reaching the fluid-air outlet, for example a spray shield or fluid-air mixture channel having an extended length.

The fluid inhalation device is configured to deliver an atomized liquid (alone or mixed with vapor from the liquid) containing one or more agents including phytochemicals, terpenes, psychoactive agents, drugs, nutraceuticals, plant extract, fragrances, flavorings, and other desirable agents, or mixtures thereof, to the mouth, tongue, throat, or lungs of a user. Examples of such agents includes terpenes such as CBD, THC, and limonene; alkaloids such as nicotine; flavorings such as menthol and vanillin; plant extracts including *cannabis* extracts; psychoactive agents such as ethanol and caffeine; nicotine fluids, essential oils, plant isolate fluids, *cannabis* fluids, and any ingredients thereof; and drugs such as steroids, bronchodilators (such as albuterol), stimulants, decongestants, vasoconstriction agents, antibiotics, anesthetics and NSAIDs. The compositions are preferably liquid with a concentration chosen to deliver the desired amount to the user. For example, the liquids currently used with vaping devices, such as those which contain nicotine and/or cannabinoids (such as CBD and THC), may be used in the fluid inhalation device. The concentration of nicotine in the liquid may be 3 mg/ml to 20 mg/ml. The concentration of CBD and/or THC may be 1 mg/ml to 50 mg/ml. Other agents, such as those described above, may be present in the liquid at a concentration of, for example, 0.1 mg/ml to 100 mg/ml.

Carriers and additives which may be present in the liquids for use with the fluid inhalation device include water; alcohols such as ethanol; glycols such as propylene glycol; sweeteners (including sugars such a sucrose, fructose, glucose and xylitol); glycerin; vegetable oils; salts such as sodium chloride; pH adjusting agents such as acetic acid and sodium bicarbonate; pharmaceutically acceptable excipients and carriers; ingredients commonly used in vaping fluids; other agents which are generally regarded as safe (GRAS); Class 3 solvents listed in "ICH guidance for industry Q3C Impurities: Residual Solvents" and mixtures and combinations thereof. Preferred components of the liquid include 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water, xylitol, and mixtures of 2, 3, 4, 5 or 6, or more thereof; each of which may be present in an amount by weight of 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 and 99%, including all ranges therebetween for each component. Preferably, the liquid composition also contains nicotine and/or cannabinoids (preferably, CBD and/or THC, such delta-9-THC and/or delta-8-THC).

The device may be made by additive manufacturing (often referred to as 3-D printing), from different materials including plastics (such as nylon, polyethylene, polypropylene, epoxy, polyurethanes, polystyrenes, polycarbonate, copolymers and combinations thereof), metals such as aluminum, ceramics and glass, and combinations thereof. Injection molding may also be used if the device is prepared as a set of components designed for injection molding and then assembled. Combinations of these manufacturing methods may also be used. Additive manufacturing may result in a monolithic device with all parts being a single unibody construction. Alternatively, individual parts, such as the removable reservoir, 152, and a removable top, 154, and the valve-activator assembly, 150, may be made as an attachment to the device by matching threads, with an adhesive, or by thermal bonding in the case of thermoplastic construction. The springs, when present, may be made of metal or a suitable plastic material.

A typical human male has a breath volume of about 0.5 liters (tidal volume), and so the device is configured to operate on a smaller volume of air sucked in through the fluid inhalation device. The inhalation may last less than 1 second, or may be controlled to last several seconds, including 1, 2, 3, 4, 5, 6, 7, 8, 9 or 10 seconds. The fluid inhalation device is configured for human mouth powered operation, that is operated by suction by mouth on a mouth piece at a pressure of −0.14 to −0.36 PSI, negative pressure relative to atmospheric pressure. The amount of fluid delivered to the mouth of a user by such human powered operation for a period of 1 second, is preferably 0.001 to 0.01 ml, more preferably 0.002 to 0.008 ml, most preferably 0.004 to 0.006 ml. Typical inhalation time by a user is 1 to 3 seconds. In the case of nicotine or cannabinoids, preferably the concentration of the nicotine or cannabinoids in the liquid is adjusted so that 10-18 inhalation from the device would deliver 1.0-1.8 mg of nicotine or cannabinoids to the user. This would mimic the dosage received from smoking tobacco products or *cannabis* products. In the case of nicotine, 1 ml of fluid should mimic the dosage received by a user when smoking a 20-cigarette pack.

According to Stokes' law, the drag force F on a sphere of radius r moving through a fluid of viscosity η at speed v is given by: $F=6\pi\eta rv$. Although several assumptions underlie the validity of the Stokes' law, it provides a good approximation for small droplets flowing through a fluid inhalation device under the effects of flowing air caused by human inhalation. The drag force is directly proportional to the radius of the droplet. The effects of gravity, and the momentum of the sphere, are proportional to the mass of the droplet, which for a homogenous liquid is proportional to the volume V of the droplet, which $V=4/3\pi r^3$. Furthermore, if the liquid in the droplet can evaporate under the ambient conditions, which is true for water and ethanol, the size of the droplet will shrink after formation. Droplet size in air or another gas may be measured using light scattering. Preferably, 90% of the droplets which flow through the fluid inhalation device, just prior to exiting the device have a radius of at most 100

μm, more preferably at most 50 μm, even more preferably at most 30 μm; for example, 90% of the droplets may have a radius of at most 100, 90, 80, 70, 60, 50, 40, 30, 20, 10, 5 or 1 μm, including all values and ranges therebetween.

What is claimed is:

1. A fluid inhalation device, comprising:
    a casing having therein
        a fluid reservoir,
        a fluid-air outlet connected to a top end of the fluid reservoir,
        a vacuum channel, having a bottom end connected to a bottom end of the fluid reservoir,
        an air duct, having an air inlet at a first air duct end,
        a nozzle connected to a second air duct end through a nozzle throat, and connected to the fluid reservoir through a nozzle exit,
    a top end of the vacuum channel is connected to the nozzle, and
    both of an air duct valve, and a fluid-air channel valve,
    the fluid inhalation device further comprising a valve activator, connected to both the air duct valve and the fluid-air channel valve.

2. The fluid inhalation device of claim 1, further comprising a filling port, and a filling port stem extending from the filling port.

3. The fluid inhalation device of claim 2, wherein the nozzle throat is narrower than the nozzle exit.

4. The fluid inhalation device of claim 2, wherein the device is configured for human mouth powered operation.

5. The fluid inhalation device of claim 4, further comprising a spray shield, between the nozzle exit and the fluid-air outlet.

6. The fluid inhalation device of claim 2, further comprising a mouth piece, containing the fluid-air outlet.

7. The fluid inhalation device of claim 2, wherein a fluid-air mixture channel connects the fluid-air outlet to the top end of the fluid reservoir.

8. The fluid inhalation device of claim 2, further comprising a fluid return channel connecting the air duct to the fluid reservoir.

9. The fluid inhalation device of claim 2, further comprising a spray shield, between the nozzle exit and the fluid-air outlet.

10. The fluid inhalation device of claim 9, wherein the spray shield blocks a straight line between the nozzle exit and the fluid-air outlet.

11. The fluid inhalation device of claim 2, wherein a bottom end of the fluid reservoir slopes down toward the vacuum channel bottom end.

12. The fluid inhalation device of claim 2, further comprising a closure for sealing the filling port.

13. The fluid inhalation device of claim 2, wherein the top end of the vacuum channel is connected to the nozzle between the nozzle throat and the nozzle exit.

14. The fluid inhalation device of claim 2, wherein the nozzle exit is between the fluid reservoir bottom end and the fluid reservoir top end.

15. The fluid inhalation device of aims claim 2, wherein the nozzle throat is narrower than the air duct.

16. The fluid inhalation device of claim 2, wherein the fluid inhalation device delivers 0.001 to 0.01 ml of fluid under a suction pressure of −0.14 to −0.36 PSI, negative pressure relative to atmospheric pressure, in 1 second.

17. The fluid inhalation device of claim 2, wherein the fluid inhalation device is monolithic.

18. The fluid inhalation device of claim 2, further comprising a valve-activator assembly, comprising the valve activator, 2 valves, and at least one spring for biasing the 2 valves.

19. The fluid inhalation device of claim 2, comprising:

a removable top containing the fluid-air outlet, and a removable reservoir containing at least a portion of the fluid reservoir, wherein the removable top and the removable reservoir are adapted to attach together.

20. The fluid inhalation device of claim 19, wherein the removable reservoir comprises fluid, and a breakable seal maintaining the liquid within the removable reservoir.

21. The fluid inhalation device of claim 2, further comprising a fluid in the fluid reservoir.

22. The fluid inhalation device of claim 21, wherein the liquid contained therein has a volume of 0.5 to 5 ml.

23. The fluid inhalation device of claim 22, wherein the fluid in the fluid reservoir comprises:

(a) at least one member selected from the group consisting of 1-butanol, 1-pentanol, 1-propanol, 2-butanol, 2-methyl-1-propanol, 2-propanol, 3-methyl-1-butanol, acetaldehyde, acetic acid, acetoin, acetone, alcohols, anisole, benzaldehyde, butyl acetate, carvone, cinnamaldehyde, decanal, diacetyl, dimethyl sulfoxide, ethanol, ethyl acetate, ethyl butyrate, ethyl ether, ethyl formate, ethyl vanillin, eugenol, formic acid, fructose, glucose, glycerin, glycols, heptane, isobutyl acetate, isopropyl acetate, limonene, linalool, methyl acetate, methyl ethyl ketone, pentane, propyl acetate, propylene glycol, salts, sodium bicarbonate, sodium chloride, sucrose, sugars, sweeteners, tert-butyl methyl ether, tocopherol acetate, triacetin, triethylamine, vegetable oils, water and xylitol, and (b) at least one member selected from the group consisting of nicotine, THC and CBD.

24. A method of consuming fluid contained within the fluid inhalation device of claim 2, comprising sucking on the mouth piece.

25. The fluid inhalation device of claim 1, further comprising a mouth piece containing the fluid-air outlet.

\* \* \* \* \*